United States Patent
Eismann et al.

(10) Patent No.: US 11,617,551 B2
(45) Date of Patent: Apr. 4, 2023

(54) X-RAY DETECTOR UNIT HAVING AT LEAST ONE ANALYSIS UNIT AND AN ADJUSTABLE VOLTAGE SUPPLY AND METHOD FOR OPERATING AN X-RAY DETECTOR UNIT

(71) Applicant: Siemens Healthcare GmbH, Erlangen (DE)

(72) Inventors: Alfons Eismann, Pinzberg (DE); Stefan Lechner, Pommersfelden (DE); Thomas Hilderscheid, Altdorf (DE); Stefan Hartmann, Eggolsheim (DE); Peter Kaemmerer, Schnaittach (DE); Waseem Haider, Erlangen (DE); Michael Grafberger, Bamberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/552,420

(22) Filed: Dec. 16, 2021

(65) Prior Publication Data
US 2022/0202385 A1   Jun. 30, 2022

(30) Foreign Application Priority Data
Dec. 28, 2020 (DE) ............... 10 2020 216 576.9

(51) Int. Cl.
*A61B 6/00* (2006.01)
*A61B 6/03* (2006.01)
(Continued)

(52) U.S. Cl.
CPC .......... *A61B 6/4208* (2013.01); *A61B 6/03* (2013.01); *A61B 6/032* (2013.01); *A61B 6/42* (2013.01);
(Continued)

(58) Field of Classification Search
CPC ......... A61B 6/032; A61B 6/035; A61B 6/037; A61B 6/42; A61B 6/4208; A61B 6/4233;
(Continued)

(56) References Cited

U.S. PATENT DOCUMENTS 4,994,965 A * 2/1991 Crawford ............. G06T 11/005
                                                    324/309
5,943,388 A * 8/1999 Tümer ................ G01V 5/0041
                                                    378/98.9
(Continued)

FOREIGN PATENT DOCUMENTS

CN      101507609 A      8/2009
CN      103765244 A      4/2014
(Continued)

OTHER PUBLICATIONS

German Office Action and English translation thereof dated Sep. 7, 2021.
(Continued)

*Primary Examiner* — Allen C. Ho
(74) *Attorney, Agent, or Firm* — Harness, Dickey & Pierce, P.L.C.

(57) ABSTRACT

An X-ray detector unit is disclosed. In an embodiment, the X-ray detector unit includes: at least one analysis unit to process electrical signals delivered from a coupled converter unit and operatable by an operating voltage; an adjustable voltage supply, coupled to the at least one analysis unit, to provide an adjustable supply voltage; an identification unit, assigned to the at least one analysis unit, to provide identification information about the at least one analysis unit in a readable manner; and a communication unit, coupled to the adjustable voltage supply, to read the identification information provided from the identification unit, and based upon the identification information provided, to adjust the adjust- (Continued)

able voltage supply to equate the provided supply voltage to the operating voltage of the at least one analysis unit.

17 Claims, 2 Drawing Sheets

(51) Int. Cl.
 *G01T 1/20* (2006.01)
 *G01T 1/208* (2006.01)
 *G01T 1/24* (2006.01)
(52) U.S. Cl.
 CPC .......... *A61B 6/4233* (2013.01); *A61B 6/4241* (2013.01); *A61B 6/4266* (2013.01); *A61B 6/4275* (2013.01); *A61B 6/52* (2013.01); *A61B 6/5205* (2013.01); *G01T 1/20* (2013.01); *G01T 1/2006* (2013.01); *G01T 1/2018* (2013.01); *G01T 1/20184* (2020.05); *G01T 1/24* (2013.01); *G01T 1/247* (2013.01)
(58) Field of Classification Search
 CPC ....... A61B 6/4241; A61B 6/52; A61B 6/5205; A61B 6/4266; A61B 6/4275; G01T 1/20; G01T 1/2006; G01T 1/2018; G01T 1/20181; G01T 1/20182; G01T 1/20184; G01T 1/24; G01T 1/242; G01T 1/243; G01T 1/247; G01T 1/249
 USPC .............. 378/5, 19, 91, 98.8, 98.9, 98.11, 4; 250/370.09
 See application file for complete search history.

(56) References Cited

U.S. PATENT DOCUMENTS

| | | | |
|---|---|---|---|
| 6,054,846 A | 4/2000 | Castleman | |
| 7,049,601 B2* | 5/2006 | Agano | H01L 27/14658 250/370.09 |
| 7,421,063 B2* | 9/2008 | Takenaka | H04N 5/378 378/91 |
| 7,796,735 B2* | 9/2010 | Yi | G03B 42/02 378/116 |
| 8,476,594 B2* | 7/2013 | Frach | G01T 1/2985 250/363.04 |
| 8,536,535 B2* | 9/2013 | Amitani | H04N 5/32 250/370.09 |
| 8,569,683 B2* | 10/2013 | Freiburger | G01T 1/40 250/363.01 |
| 8,921,754 B2* | 12/2014 | Frach | G01T 1/40 250/214 AG |
| 9,254,113 B2* | 2/2016 | Kim | A61B 6/502 |
| 9,383,459 B2* | 7/2016 | Atsuta | G01T 1/208 |
| 9,423,515 B2* | 8/2016 | Roessl | G01T 1/24 |
| 9,588,231 B2* | 3/2017 | Graf | G01T 1/175 |
| 9,588,239 B2* | 3/2017 | Abraham | A61B 6/4241 |
| 9,675,309 B2* | 6/2017 | Kim | A61B 6/4494 |
| 9,835,735 B2* | 12/2017 | Preston | G01T 1/02 |
| 9,980,683 B2* | 5/2018 | Onouchi | A61B 6/035 |
| 10,001,567 B2* | 6/2018 | Roessl | G01T 1/24 |
| 10,058,297 B2* | 8/2018 | Park | A61B 6/461 |
| 10,193,635 B2* | 1/2019 | Wang | H01L 31/02027 |
| 10,305,605 B2* | 5/2019 | Sun | H04B 10/032 |
| 10,324,201 B2* | 6/2019 | Groepl | H03M 1/662 |
| 10,345,458 B2* | 7/2019 | Chen | G01T 1/2018 |
| 10,444,380 B2* | 10/2019 | Graf | G01T 1/175 |
| 10,470,723 B2* | 11/2019 | Herrmann | H01L 27/14676 |
| 10,638,987 B2* | 5/2020 | Eichenseer | G01T 1/00 |
| 10,665,003 B2* | 5/2020 | Polster | A61B 6/4241 |
| 10,667,774 B2* | 6/2020 | Kato | A61B 6/4233 |
| 10,682,104 B2* | 6/2020 | Flohr | A61B 6/545 |
| 10,713,822 B2* | 7/2020 | Lee | A61B 6/4291 |
| 10,743,834 B2* | 8/2020 | Kato | A61B 6/405 |
| 10,905,388 B2* | 2/2021 | Kojima | A61B 6/4241 |
| 10,976,448 B2* | 4/2021 | Eismann | G01T 1/161 |
| 11,064,966 B2* | 7/2021 | Iwakiri | A61B 6/56 |
| 11,076,823 B2* | 8/2021 | Tamura | A61B 6/035 |
| 11,109,823 B2* | 9/2021 | Flohr | A61B 6/504 |
| 11,229,413 B1* | 1/2022 | Lai | A61B 6/032 |
| 11,278,255 B2* | 3/2022 | Flohr | A61B 6/482 |
| 2009/0207974 A1 | 8/2009 | Yi | |
| 2014/0183371 A1 | 7/2014 | Roessl et al. | |
| 2015/0198724 A1 | 7/2015 | Graf et al. | |
| 2016/0231437 A1 | 8/2016 | Chaudhury et al. | |
| 2016/0273959 A1 | 9/2016 | Wang | |
| 2017/0285186 A1 | 10/2017 | Roessl et al. | |
| 2018/0081070 A1 | 3/2018 | Graf et al. | |
| 2018/0160989 A1 | 6/2018 | Herrmann | |
| 2018/0269987 A1 | 9/2018 | Sun et al. | |
| 2019/0346574 A1 | 11/2019 | Eismann et al. | |

FOREIGN PATENT DOCUMENTS

| | | |
|---|---|---|
| CN | 105852891 A | 8/2016 |
| CN | 106030345 A | 10/2016 |
| CN | 106033225 A | 10/2016 |
| CN | 107809953 A | 3/2018 |
| CN | 107204811 B | 7/2020 |
| DE | 102016217993 A1 | 3/2018 |

OTHER PUBLICATIONS

German Decision to Grant and English translation thereof dated Sep. 20, 2021.

* cited by examiner

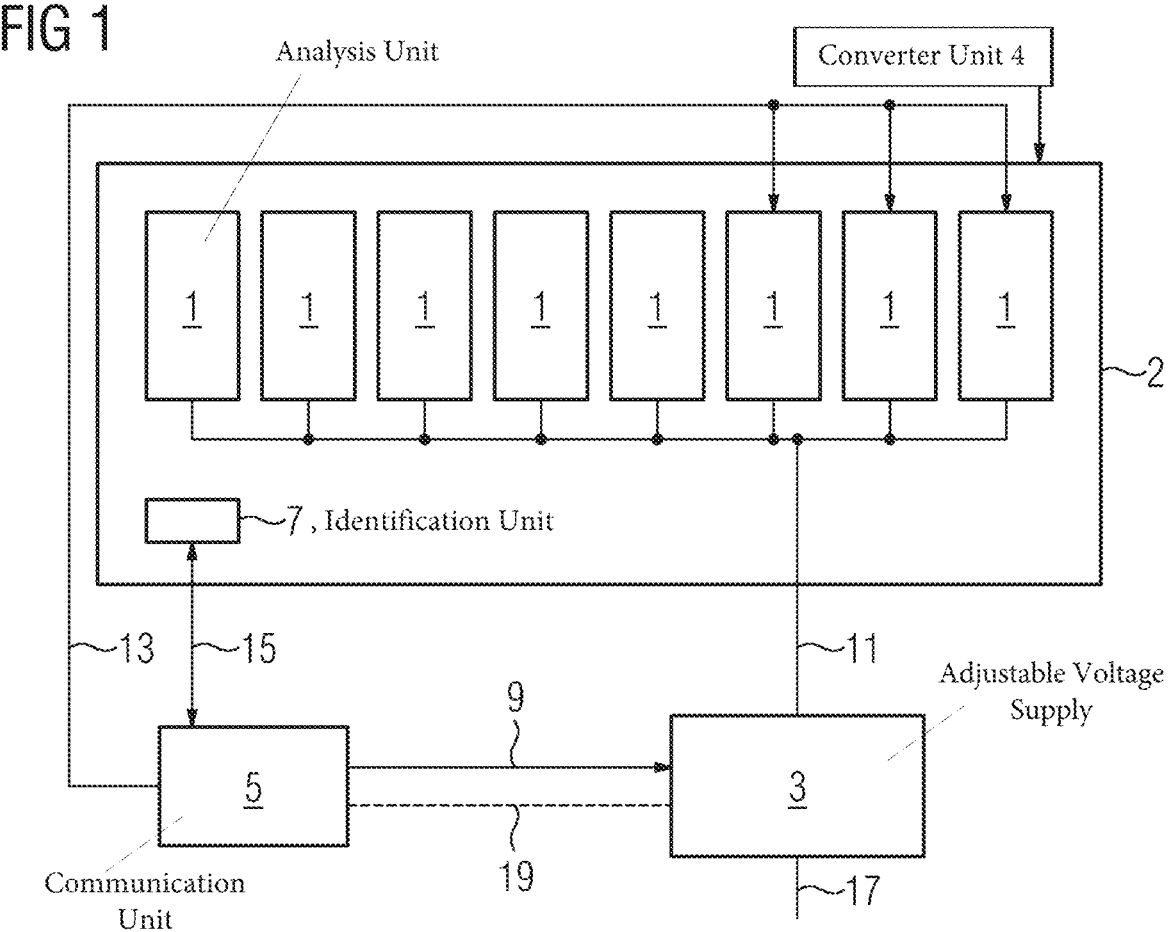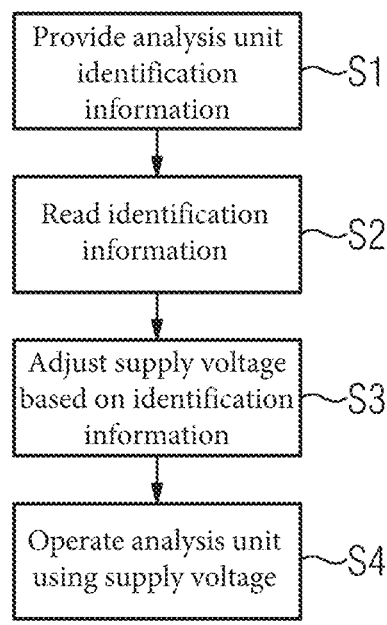

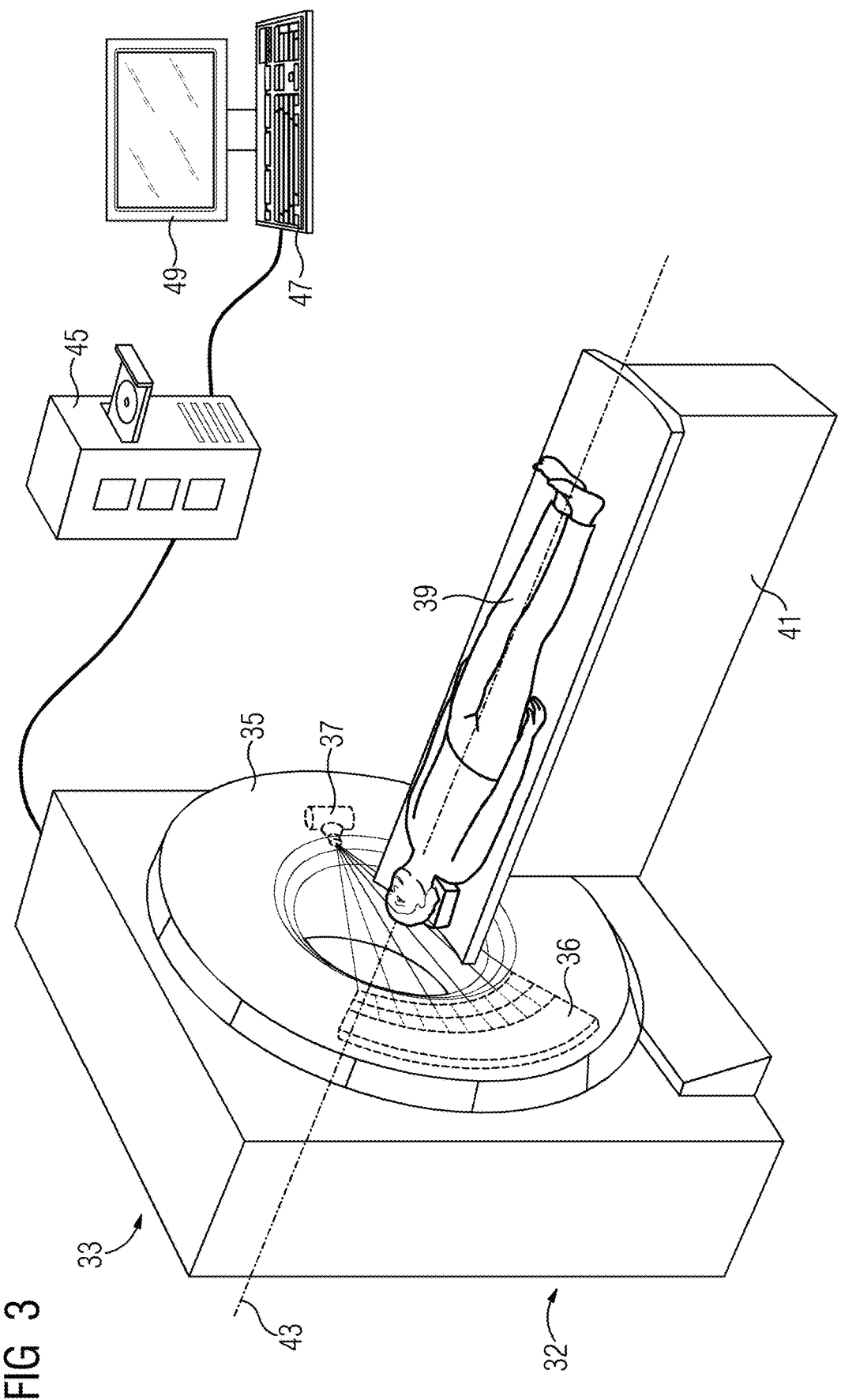

X-RAY DETECTOR UNIT HAVING AT LEAST ONE ANALYSIS UNIT AND AN ADJUSTABLE VOLTAGE SUPPLY AND METHOD FOR OPERATING AN X-RAY DETECTOR UNIT

PRIORITY STATEMENT

The present application hereby claims priority under 35 U.S.C. § 119 to German patent application number DE 102020216576.9 filed Dec. 28, 2020, the entire contents of which are hereby incorporated herein by reference.

FIELD

Example embodiments of the invention generally relate to an X-ray detector unit having an adjustable voltage supply, to an X-ray detector, to an associated medical imaging device, and to an associated method for operating an X-ray detector unit.

BACKGROUND

X-ray detectors are used in numerous imaging applications. For instance, X-ray detectors are used in computed tomography apparatuses in medical imaging in order to produce a tomographic X-ray image dataset of a region of interest of a patient. In the case of a computed tomography device (CT device), for example, in order to acquire image data in three spatial dimensions, an X-ray source and a detector apparatus working jointly therewith rotate about a rotational axis and about an examination object to be examined, for instance a patient. During the rotational movement, measurement data is acquired from different projection angles. The (projection) measurement data constitutes a multiplicity of projections containing information about the attenuation of the radiation through the examination object from different projection angles. A two-dimensional sectional image or sectional images, or a three-dimensional volumetric image, of the examination object can be computed from these projections, for instance using what is known as filtered backprojection or other suitable reconstruction techniques, for example an iterative reconstruction algorithm.

Counting, direct-converting X-ray detectors or integrating, indirect-converting X-ray detectors can be used in X-ray imaging. In direct-converting X-ray detectors, the X-ray radiation or the photons can be converted into electrical pulses by a suitable converter material. Examples of materials that can be used as the converter material are CdTe, CZT, CdZnTeSe, CdTeSe, CdMnTe, InP, $TlBr_2$, $HgI_2$, GaAs or other materials. The electrical pulses can be evaluated by electronic circuits of an analysis unit, for instance in the form of an integrated circuit (application-specific integrated circuit, ASIC). In counting X-ray detectors, the incident X-ray radiation can be measured by counting the electrical pulses triggered by the absorption of X-ray photons in the converter material. In addition, the height of the electrical pulse is usually proportional to the energy of the absorbed X-ray photon. Spectral information can hence be extracted by comparing the height of the electrical pulse with a threshold value. In indirect-converting X-ray detectors, the X-ray radiation or the photons can be converted into light by a suitable converter material, and into electrical pulses by optically coupled photodiodes. Scintillators, for instance GOS ($Gd_2O_2S$), CsJ, YGO or LuTAG, are often used as the converter material. Again, the generated electrical signals are processed further by an analysis unit comprising electronic circuits. Scintillators are used in particular in medical X-ray imaging in the energy range up to 1 MeV.

SUMMARY

The analysis units for processing further the generated electrical signals in X-ray detectors are supplied with voltage by a voltage supply in order to operate the X-ray detector. The inventors have discovered that it is important here to avoid applying voltage levels that are too low or too high, in order to prevent damage or problems during configuration and operation. The inventors have further discovered that different voltage levels may also be needed for different analysis units.

At least one embodiment of the invention provides an improved X-ray detector unit that better guarantees safe operation of the X-ray detector unit.

The claims and the description below present further advantageous embodiments and developments of the invention, some of which are inventive in their own right.

At least one embodiment of the invention provides an X-ray detector unit comprising at least one analysis unit which is designed to process electrical signals delivered from a coupled converter unit and can be operated by an operating voltage. The X-ray detector unit also comprises an adjustable voltage supply coupled to the at least one analysis unit and designed to provide an adjustable supply voltage. The X-ray detector unit further comprises an identification unit assigned to the at least one analysis unit and designed to provide identification information about at least one analysis unit in a readable manner. The X-ray detector unit according to at least one embodiment of the invention also comprises a communication unit coupled to the adjustable voltage supply and designed to read the provided identification information from the identification unit, and on the basis thereof, to adjust the adjustable voltage supply such that the provided supply voltage equates to the operating voltage of the at least one analysis unit. In other words, the provided supply voltage can be provided in an adjustable manner, and the communication unit is designed to adjust the adjustable voltage supply such that the supply voltage that can be provided by the adjustable voltage supply is adjusted to the operating voltage and is provided for operation of the analysis unit.

At least one embodiment of the invention provides an X-ray detector comprising at least two X-ray detector units according to an embodiment, wherein the adjustable voltage supply of the first of the two X-ray detector units provides a first supply voltage, adjusted to the operating voltage of the at least one analysis unit of the first X-ray detector unit, and the adjustable voltage supply of the second of the two X-ray detector units provides a second supply voltage, adjusted to the operating voltage of the at least one analysis unit of the second X-ray detector unit.

At least one embodiment of the invention provides a medical imaging device comprising at least one X-ray detector unit according to one of the above-described embodiments or comprising an above-described X-ray detector, and an X-ray source opposite thereto, designed to shine X-ray radiation onto the X-ray detector unit or the X-ray detector.

At least one embodiment of the invention provides a method for operating an X-ray detector unit, for example according to one of the embodiments described above. The method comprises the steps of providing, reading, automatically adjusting, and operating. In the providing step, an identification unit assigned to the at least one analysis unit provides identification information about the at least one analysis unit. In the reading step, the communication unit reads the identification information from the identification unit. In the step of automatically adjusting, a providable supply voltage of the adjustable voltage supply coupled to the at least one analysis unit is adjusted by the communication unit based upon the identification information provided, so that the provided supply voltage equates to the operating voltage of the at least one analysis unit. In the step of operating the at least one analysis unit, the at least one analysis unit is operated using the supply voltage provided by the adjustable voltage supply.

At least one embodiment of the invention provides an X-ray detector unit comprising:

at least one analysis unit to process electrical signals delivered from a coupled converter unit and operatable by an operating voltage;

an adjustable voltage supply, coupled to the at least one analysis unit, to provide an adjustable supply voltage;

an identification unit, assigned to the at least one analysis unit, to provide identification information about the at least one analysis unit in a readable manner; and a communication unit, coupled to the adjustable voltage supply, to read the identification information provided from the identification unit, and based upon the identification information provided, to adjust the adjustable voltage supply to equate the provided supply voltage to the operating voltage of the at least one analysis unit.

At least one embodiment of the invention provides an X-ray detector, comprising:

at least two X-ray detector units, each of the at least two X-ray detector units including the X-ray detector unit of claim 1, wherein the adjustable voltage supply of a first X-ray detector unit of the at least two X-ray detector units is designed to provide a first supply voltage, adjusted to the operating voltage of the at least one analysis unit of the first X-ray detector unit, and the adjustable voltage supply of a second X-ray detector unit of the two X-ray detector units is designed to provide a second supply voltage, adjusted to the operating voltage of the at least one analysis unit of the second X-ray detector unit.

At least one embodiment of the invention provides a medical imaging device, comprising:

at least one X-ray detector unit, each at least one X-ray detector unit including the X-ray detector unit of an embodiment; and an X-ray source opposite the at least one X-ray detector unit, designed to shine X-ray radiation onto the at least one X-ray detector unit.

At least one embodiment of the invention provides a method for operating an X-ray detector unit including at least one analysis unit to process electrical signals delivered from a coupled converter unit and operatable by an operating voltage, the method comprising:

providing identification information about the at least one analysis unit via an identification unit assigned to the at least one analysis unit;

reading the identification information from the identification unit via a communication unit;

automatically adjusting, via the communication unit, a providable supply voltage of an adjustable voltage supply coupled to the at least one analysis unit based upon the identification information provided, to equate supply voltage provided to the operating voltage of the at least one analysis unit; and operating the at least one analysis unit using the supply voltage provided by the adjustable voltage supply.

At least one embodiment of the invention provides a medical imaging device, comprising:

the X-ray detector of an embodiment, and an X-ray source opposite the at least one X-ray detector unit of the X-ray detector, designed to shine X-ray radiation onto the at least one X-ray detector unit of the X-ray detector.

BRIEF DESCRIPTION OF THE DRAWINGS

The invention is described below using example embodiments with reference to the accompanying figures. Schematic, highly simplified diagrams that are not necessarily to scale appear in the figures. The same reference signs are used for the same features in different figures, in which:

FIG. 1 shows a schematic diagram of an X-ray detector unit according to an embodiment of the invention;

FIG. 2 shows a schematic diagram of a method according to an embodiment of the invention for operating an X-ray detector unit; and FIG. 3 shows a schematic diagram of an example embodiment of a medical imaging device.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector unit comprising at least one analysis unit which is designed to process electrical signals delivered from a coupled converter unit and can be operated by an operating voltage. The X-ray detector unit also comprises an adjustable voltage supply coupled to the at least one analysis unit and designed to provide an adjustable supply voltage. The X-ray detector unit further comprises an identification unit assigned to the at least one analysis unit and designed to provide identification information about at least one analysis unit in a readable manner. The X-ray detector unit according to at least one embodiment of the invention also comprises a communication unit coupled to the adjustable voltage supply and designed to read the provided identification information from the identification unit, and on the basis thereof, to adjust the adjustable voltage supply such that the provided supply voltage equates to the operating voltage of the at least one analysis unit. In other words, the provided supply voltage can be provided in an adjustable manner, and the communication unit is designed to adjust the adjustable voltage supply such that the supply voltage that can be provided by the adjustable voltage supply is adjusted to the operating voltage and is provided for operation of the analysis unit.

In particular this also includes that the at least one analysis unit can be operated by more than one operating voltage, and the adjustable voltage supply coupled to the at least one analysis unit is designed to provide more than one adjustable supply voltage. The communication unit coupled to the adjustable voltage supply can then be designed in particular to read the provided identification information from the identification unit, and on the basis thereof, to adjust the adjustable voltage supply such that the adjusted provided supply voltages each equate to the respective operating voltages of the at least one analysis unit.

The analysis unit can be in the form of an integrated circuit, for example. In particular, the analysis unit can be in the form of an application-specific integrated circuit (ASIC). The analysis unit can comprise a multiplicity of pixel electronic circuits, with each pixel electronic circuit of the multiplicity of pixel electronic circuits being designed to process the delivered electrical signals into a digital pixel-measurement signal. A multiplicity of pixel electronic circuits allow spatially resolved and parallel processing of the delivered electrical signals from the converter unit. The analysis unit can be designed in particular to process further, in particular to digitize, for instance via an A/D converter (analog-to-digital converter), the electrical signals delivered from the coupled converter unit. In addition, the analysis unit can also have further circuit elements, for instance a signal amplifier or a comparator. In particular, each pixel electronic circuit of a multiplicity of pixel electronic circuits comprised by an analysis unit can comprise a signal amplifier, a comparator or a digitization circuit-element.

The coupled converter unit can be designed in particular to convert incident X-ray radiation into electrical signals. A converter unit coupled to the analysis unit can be in the form of a direct-converting converter unit comprising a direct-converting converter material. The converter unit can also be in the form of an indirect-converting converter unit. In this case, the converter unit can comprise, for example, a scintillator material and a number of photodiodes coupled thereto.

In at least one embodiment, the identification unit provides identification information about the at least one analysis unit. The identification information may comprise information about the type of analysis unit. The identification information may comprise information relating to setting parameters for the analysis unit, or from which it is possible to derive setting parameters for the analysis unit. A setting parameter may be, in particular, the operating voltage to be set for operation of the at least one analysis unit, i.e. to be applied to the analysis unit.

The identification unit can comprise for this a memory unit, in particular a non-volatile, i.e. permanent, memory unit, on which is stored the identification information in a retrievable manner. For example, a memory unit may comprise a flash memory, an SSD (solid state disk) or a ROM (read-only memory). The identification unit may have an interface that allows reading, i.e. retrieval, of the identification information stored on the memory unit. An interface may be a hardware interface (for instance PCI bus, USB or FireWire).

The communication unit can also be referred to as an intelligent communication unit, which can communicate with the identification unit and the adjustable voltage supply and process information retrieved from the identification unit. In particular, the communication unit can read and process the identification information from the identification unit, and adjust the adjustable voltage supply on the basis thereof. The processing of the identification information can comprise deriving, based upon the identification unit, an adjustment parameter, i.e. a setting parameter, for the adjustable voltage supply, so that the supply voltage provided by the adjustable voltage supply equates to the operating voltage of the at least one analysis unit. The processing can equate to translating the read identification information into an adjustment parameter for the adjustable voltage supply. For example, the derived adjustment parameter can be communicated to the adjustable voltage supply via a suitable interface, for instance an I2C interface (acronym for Inter-Integrated Circuit interface). The communication unit may be, for example, a computer, a microcontroller or an integrated circuit. The communication unit may have hardware elements or software elements, for instance a microprocessor or what is known as an FPGA (field programmable gate array).

The adjustable voltage supply can be adjustable in particular in the manner that, based upon an input voltage, it can output, i.e. provide, as a supply voltage different output voltages, depending on the setting. For example, the adjustable voltage supply can use one or more voltage converters to step down a DC input voltage to a DC output voltage, which in particular can be set. For instance, an input voltage in the range of several hundred Volts can be stepped down and set to an output voltage of less than 7V, preferably less than 6V, for example between 2V and 6V, specifically about 2.5V, by the adjustable voltage supply. An input voltage may be, for example, in the range of 200V-500V, specifically 360V for instance. The conversion of the input voltage into an output voltage can be performed in the adjustable voltage supply in a plurality of steps. For example, there may be provided a pre-converter, which converts the input voltage to an intermediate voltage, and one or more post-regulators, which regulate the intermediate voltage to the output voltage. The voltage supply is preferably also equipped to stabilize the provided supply voltage, i.e. to hold the provided supply voltage at a voltage level that is as constant as possible and preferably low-noise. For example, stabilization to +/−3% of the nominal output value is desirable. The analysis unit is thereby able to perform signal detection particularly precisely.

A deployed voltage converter can be in the form of a DC-DC/AC-DC converter or transformer. In particular, a post-regulator can preferably be embodied as a linear regulator, which is equipped in particular to produce from the intermediate voltage a voltage level that is as stable as possible and in particular is low-noise. A voltage converter, in particular a pre-converter, can also be in the form of a switching regulator, for example.

Designing the adjustable voltage supply to be adjustably set can be achieved in particular in that at least one voltage converter in the adjustable voltage supply is designed to be adjustably set. The setting of the at least one voltage converter can then be adjusted by the communication unit.

In at least one embodiment, the X-ray detector unit according to the invention advantageously allows the voltage supply to adjust, in particular automatically, the provided supply voltage, which equates to the operating voltage of the at least one analysis unit. In addition, the type of the analysis unit, and hence its operating voltage, can be retrieved or derived explicitly by way of the identification information. Incorrect settings can advantageously be avoided and thus allow safe operation of the X-ray detector unit. In addition, an X-ray detector unit having different types of analysis units can advantageously be operated without the need to modify or replace the voltage supply or the communication unit. For example, existing systems relating to the voltage supply can be used in a redesign of the analysis unit. This can advantageously reduce development costs, logistical costs and/or storage costs. In addition, whenever such changes are made, the identification of the analysis units employed and the automatic adjustment of the voltages provided improve the assurance of safe operation.

In a preferred embodiment, the adjustable voltage supply can provide a supply voltage that can be set between 1V and 7V. For example, the adjustable voltage supply can be adjusted at least to voltage levels between 2V and 6V. This advantageously equates to typical operating voltages of analysis units that can be used in X-ray detector units.

According to a development of the X-ray detector unit, the communication unit is designed to derive an adjustment parameter for adjusting the adjustable voltage supply based upon the identification information and a query to a look-up table (LUT) stored in a memory unit of the communication unit. For example, a memory unit may comprise RAM (random access memory), or a flash memory, an SSD (solid state disk) or a ROM (read-only memory). The memory unit is preferably writable at least when the X-ray detector unit is not operating, making it easy to update the look-up table. This allows an update or expansion of the look-up table to new types of analysis unit. This advantageously corresponds to a particularly simple way to implement transferring the employed analysis unit, and the settings required for the operating voltage, to adjustment parameters of the adjustable voltage supply, and facilitating adjustment of the adjustable voltage supply to the analysis unit currently being used.

In a development of the X-ray detector unit according to at least one embodiment of the invention, the communication unit is also designed to activate the at least one analysis unit once the supply voltage provided by the adjustable voltage supply is adjusted to the operating voltage of the at least one analysis unit.

In this embodiment variant, the communication unit is coupled, in particular for signal communication, to the at least one analysis unit. In particular, an activation signal can be communicated to the at least one analysis unit. Advantageously, as a result of the control unit being designed to activate, i.e. enable, the at least one analysis unit only once the operating voltage needed for the analysis unit is set and can be provided, it is possible to achieve reliable booting and optimum hardware configuration of the analysis unit. For instance, too low a voltage level can cause problems in configuring the electronics. Furthermore, too high a voltage level can cause damage. Advantageously, automatic activation of the analysis unit is allowed as soon as the conditions for operation are optimal.

In addition, the adjustable voltage supply is also designed to provide a second voltage, which differs from the operating voltage of the at least one analysis unit, for operating the communication unit.

The ability of the adjustable voltage supply to generate different (operating) voltages simplifies the voltage distribution within the X-ray detector unit, with the result that a single main voltage can be provided for supplying the voltage to all the electrical loads of the X-ray detector unit. In particular in more complex systems comprising one or more X-ray detector units, it can hence be achieved that just one single main voltage can be provided by a central voltage supply unit for supplying the voltage to all the electrical loads in the system, and can be converted locally and close to the load by the adjustable voltage supply for the loads of the particular X-ray detector unit. This can avoid separate supply lines for different loads. The respective operating voltages, in particular the operating voltage of the analysis unit and the second operating voltage, can moreover be produced by the adjustable voltage supply directly at the particular load or at a small spatial distance therefrom. It is thereby possible to reduce the expenditure on lines (quantity and length of the various electrical lines for the different voltages).

For example, the adjustable voltage supply has a cascaded structure for the voltage conversion by a pre-converter and one or more post-regulators, as already described previously. The second operating voltage can then be tapped from between the pre-regulator and the (if applicable, first) post-regulator, or between two of, if applicable, a plurality of post-regulators.

In a development of the X-ray detector unit according to at least one embodiment of the invention, the X-ray detector unit comprises a plurality of analysis units which can be operated by the operating voltage, wherein the adjustable voltage supply is designed to provide the operating voltage for the plurality of analysis units. The adjustable voltage supply is then coupled to each of the plurality of analysis units via a line, so that the provided supply voltage, adjusted to the operating voltage of the respective analysis units, can be provided for each of the analysis units. The plurality of analysis units preferably comprises in this case identical analysis units that are operated by the same operating voltage. An identification unit is preferably linked to the plurality of identical analysis units. Large-area X-ray detector units can advantageously be achieved with a smaller number of voltage supplies having to be provided.

At least one embodiment of the invention also relates to an X-ray detector comprising at least two X-ray detector units according to an embodiment, wherein the adjustable voltage supply of the first of the two X-ray detector units provides a first supply voltage, adjusted to the operating voltage of the at least one analysis unit of the first X-ray detector unit, and the adjustable voltage supply of the second of the two X-ray detector units provides a second supply voltage, adjusted to the operating voltage of the at least one analysis unit of the second X-ray detector unit.

The first X-ray detector unit and the second X-ray detector unit preferably comprise identical analysis units that can be operated by the same operating voltage. It is also conceivable, however, that different analysis units are used, and therefore the supply voltage provided by the adjustable voltage supply of the first of the two X-ray detector units differs from the supply voltage provided by the adjustable voltage supply of the second of the two X-ray detector units. A versatile X-ray detector, in particular also a versatile interchangeability of X-ray detector units in an X-ray detector, is advantageously made possible while identical and possibly existing components relating to the voltage supply can still be used. Safe operation is guaranteed at the same time. Advantageously, conversion close to the load can also be achieved by providing an adjustable voltage supply for each X-ray detector unit, which may comprise a plurality of analysis units.

At least one embodiment of the invention also relates to a medical imaging device comprising at least one X-ray detector unit according to one of the above-described embodiments or comprising an above-described X-ray detector, and an X-ray source opposite thereto, designed to shine X-ray radiation onto the X-ray detector unit or the X-ray detector.

All the embodiment variants described above in connection with the X-ray detector unit according to the invention can also be implemented correspondingly in the X-ray detector. The description of embodiments relating to the X-ray detector unit and the aforementioned advantages of the analysis unit can also be applied accordingly to the X-ray detector.

For acquiring an X-ray image dataset via the medical imaging device, the object to be imaged can be positioned between the X-ray source and the X-ray detector unit or the X-ray detector, and the X-ray source can beam radiation through the object.

In particular, the medical imaging device can be in the form of a computed tomography device. The medical imaging device may also be in the form of a SPECT or PET system. It may also be in the form of a C-arm X-ray device and/or DynaCT system, however, or else have a different design.

All the embodiment variants described above in connection with the X-ray detector unit according to embodiments of the invention or the X-ray detector according to embodiments of the invention can also be implemented accordingly in the medical imaging device comprising at least one X-ray detector unit according to embodiments of the invention or an X-ray detector according to embodiments of the invention. The description relating to the at least one X-ray detector unit according to embodiments of the invention or to the X-ray detector according to embodiments of the invention, and the aforementioned features and advantages can also be applied accordingly to the medical imaging device according to embodiments of the invention.

At least one embodiment of the invention also relates to a method for operating an X-ray detector unit, for example according to one of the embodiments described above. The method comprises the steps of providing, reading, automatically adjusting, and operating. In the providing step, an identification unit assigned to the at least one analysis unit provides identification information about the at least one analysis unit. In the reading step, the communication unit reads the identification information from the identification unit. In the step of automatically adjusting, a providable supply voltage of the adjustable voltage supply coupled to the at least one analysis unit is adjusted by the communication unit based upon the identification information provided, so that the provided supply voltage equates to the operating voltage of the at least one analysis unit. In the step of operating the at least one analysis unit, the at least one analysis unit is operated using the supply voltage provided by the adjustable voltage supply.

With regard to the method according to at least one embodiment of the invention, reference is made to the description of the X-ray detector unit according to at least one embodiment of the invention. The advantages of the proposed method are essentially the same as the advantages of the proposed X-ray detector unit. Features, advantages or alternative embodiments mentioned in this connection can also be applied to the method, and vice versa.

In addition, the communication unit can be designed to activate the at least one analysis unit. The method can then comprise the communication unit activating the at least one analysis unit only once the provided supply voltage is adjusted to the operating voltage of the at least one analysis unit.

In the context of the invention, features described with regard to different embodiments of the invention and/or different claim categories (method, use, device, system, arrangement, etc.) can also be combined to give further embodiments of the invention. For example, a claim relating to a device can also be developed by combining with features described or claimed in connection with a method, and vice versa. Functional features of a method can be implemented for instance by correspondingly designed object-related components. In addition to the embodiments of the invention described explicitly in this application, a person skilled in the art will be able to arrive at various further conceivable embodiments of the invention without departing from the scope of the invention defined by the claims.

The use of the indefinite article "a" or "an" does not rule out the possibility of there also being more than one of the feature concerned. In particular, if reference is made to an operating voltage of the at least one analysis unit, or to an adjustably providable supply voltage of the adjustable supply voltage, at least one operating voltage, i.e. also a plurality of operating voltages, and at least one adjustably providable supply voltage, i.e. also a plurality of supply voltages, exist, or can be provided and each adjusted to an operating voltage. The use of the expression "have" does not exclude the possibility of the terms linked by the expression "have" being identical. For example, the medical imaging device has the medical imaging device. The use of the expression "unit" does not exclude the possibility that the subject to which the expression "unit" relates has a plurality of components that are spatially separate from one another.

In the context of the present application, the expression "based upon" can be understood in particular in the sense of the expression "using". In particular, any wording, according to which a first feature is produced (or obtained, defined) based upon a second feature, does not exclude the possibility that the first feature is produced (or obtained, defined) based upon a third feature.

FIG. 1 shows a schematic diagram of an X-ray detector unit according to an embodiment of the invention.

The X-ray detector unit comprises according to an embodiment of the invention at least one analysis unit 1, which is designed to process electrical signals delivered from a coupled converter unit 4, and can be operated by at least one operating voltage. In the embodiment variant shown by way of example, the X-ray detector unit comprises a plurality of analysis units 1. The coupled converter unit 4 can be designed in particular to convert incident X-ray radiation into electrical signals, and can be in the form of a direct-converting converter unit comprising a suitable direct-converting converter material, or an indirect-converting converter unit.

The analysis units 1 of the embodiment variant shown here are in particular all of identical design at least in the sense that they can be operated by the same operating voltage. An analysis unit 1 can be in the form of an application-specific integrated circuit (ASIC), for example.

The X-ray detector unit also comprises an adjustable voltage supply 3 coupled to the at least one analysis unit 1, in this case to the plurality of analysis units 1, and designed to provide at least one adjustable supply voltage.

The X-ray detector unit further comprises an identification unit 7 assigned to the at least one analysis unit 1, in this case to the plurality of analysis units 1, and designed to provide identification information about the at least one analysis unit 1, in this case the plurality of analysis units 1, in a readable manner.

The identification unit and the analysis unit(s) 1 can be embodied as one part or can be connected to form a component. In the embodiment shown, for example, the analysis units 1 are coupled to a readout unit 2, on which is also positioned the identification unit. The readout unit 2 can be used, for example, to combine and transfer the data from the analysis units 1 to units downstream. In addition, the readout unit 2 can comprise, for example, lines 11 for feeding the supply voltage to the analysis units 1.

The adjustable voltage supply 3 is coupled via a line 11 to each analysis unit 1 in order to supply the analysis unit 1 with a voltage.

The X-ray detector unit also comprises a communication unit 5, which is coupled to the adjustable voltage supply 3 and is designed to read the provided identification information from the identification unit 7 via signal coupling 15. The communication unit 5 is additionally designed to adjust, based upon the identification information, the adjustable supply voltage via a signal coupling 9 such that the at least one provided supply voltage equates to the at least one operating voltage of the analysis unit 1.

The adjustable voltage supply 3 is adjustable in particular in the manner that, based upon an input voltage, provided via a line 17, it can output, i.e. provide, as a supply voltage a set output voltage, i.e. in particular different output voltages, depending on the setting. For example, the adjustable voltage supply 3 can use one or more voltage converters to step down a DC input voltage to a DC output voltage, which in particular can be set. For instance, an input voltage in the range of 300V-400V can be stepped down to an output voltage of less than 7V, for example between 2V and 6V, by the adjustable voltage supply 3. Specifically, it is possible to provide an input voltage of 360V, for instance via the supply line 17, which, in a first setting of the adjustable voltage supply 3, is stepped down to 2.5V, for example, and output as the supply voltage. Depending on an adjustment of the adjustable voltage supply 3, the input voltage can be converted to another value, which is different from 2.5V, and output. For example, in a second setting of the adjustable voltage supply 3, the input voltage provided via the line 17 is converted to 5.5V and output as the supply voltage. According to the invention, the communication unit 5 is designed to adjust the adjustable voltage supply 3. The adjustable voltage supply 3 is adjusted in particular such that the at least one supply voltage provided by the adjustable voltage supply 3 equates to the at least one operating voltage of the analysis unit 1.

The conversion of the input voltage into an output voltage can be performed in the adjustable voltage supply 3 in a plurality of steps. For example, there may be provided a pre-converter, which converts the input voltage to an intermediate voltage, and one or more post-regulators, which regulate the intermediate voltage to the output voltage. Designing the adjustable voltage supply 3 to be adjustably set is achieved in particular in that at least one voltage converter is designed to be adjustably set, and the setting can be adjusted by the communication unit 5.

The supply voltage that can be provided by the adjustable voltage supply 3 can preferably be provided between 1V and 7V. For example, voltage levels between 2V and 6V can be set.

According to an embodiment, the communication unit 5 can be designed to derive an adjustment parameter for adjusting the adjustable voltage supply 3 based upon the identification information and a query to a look-up table stored in a memory unit of the communication unit 5.

According to an advantageous embodiment variant, the communication unit 5 can also be designed to activate, in particular automatically, the at least one analysis unit 1, in this case in particular the plurality of analysis units 1, via a signal line 13 once the supply voltage provided by the adjustable voltage supply 3 is adjusted to the operating voltage of the analysis unit 1.

In addition, the adjustable voltage supply 3 can be designed to provide via a line 19 a second voltage, which differs from the operating voltage of the analysis unit 1, for operating the communication unit 5. For example, the adjustable voltage supply 3 has a cascaded structure for the voltage conversion by a pre-converter and one or more post-regulators. The second voltage, i.e. the operating voltage of the communication unit 5, can then be tapped from between the pre-converter and the (if applicable, first) post-regulator, or between two of, if applicable, a plurality of post-regulators. For example, the adjustable voltage supply 3 can provide an operating voltage for the communication unit in the range of 10V to 50V, specifically 24V, for instance.

FIG. 2 shows a schematic diagram of a method according to an embodiment of the invention for operating an X-ray detector unit according to one of the embodiment variants described above. The method is described below with reference to an X-ray detector unit comprising at least one analysis unit 1. The method can also be easily applied, however, to a plurality of analysis units 1, as shown for example in FIG. 1, or X-ray detector units.

In step S1, an identification unit 7 assigned to the at least one analysis unit 1 provides identification information about the at least one analysis unit 1.

In step S2, the communication unit 5 reads the identification information from the identification unit 7.

In step S3, at least one providable supply voltage of the adjustable voltage supply 3 coupled to the at least one analysis unit 1 is adjusted automatically by the communication unit 5 based upon the identification information provided, so that the at least one provided supply voltage equates to the at least one operating voltage of the at least one analysis unit 1.

In step S4, the at least one analysis unit 1 is operated using as the operating voltage the at least one supply voltage provided by the adjustable voltage supply 3.

In particular, the communication unit 5 can be designed to activate the at least one analysis unit 1. The communication unit 5 preferably activates the at least one analysis unit 1 in step S4 only once the provided supply voltage is adjusted to the operating voltage of the at least one analysis unit 1.

FIG. 3 shows an example embodiment of a medical imaging device 32 having a detection unit 36, which comprises at least one X-ray detector unit according to an embodiment of the invention, and an X-ray source 37 opposite to the detection unit 36 and hence also to the X-ray detector unit. The X-ray source 37 is designed to shine X-ray radiation onto the detection unit 36, and thus onto a converter unit 4 coupled to the at least one analysis unit 1 of the at least one comprised X-ray detector unit.

The medical imaging device 32 shown is in particular in the form of a computed tomography device. In other embodiment variants, a medical imaging device according to the invention may also be in the form of a SPECT or PET system, for instance, or a C-arm X-ray device or DynaCT system.

The computed tomography device comprises a gantry 33 having a rotor 35. The rotor 35 comprises the X-ray source 37 and the detection unit 36. The rotor 35 can rotate about the rotational axis 43. The object 39 under examination, in this case a patient, is supported on the patient couch 41 and can be moved along the rotational axis 43 by the gantry 33. In general, the object 39 can include, for example, an animal patient and/or a human patient.

The detection unit 36 can also comprise an X-ray detector having at least two X-ray detector units as described above, wherein the adjustable voltage supply 3 of the first of the two X-ray detector units provides at least one first supply voltage, adjusted to the at least one operating voltage of the at least one analysis unit 1 of the first X-ray detector unit, and the adjustable voltage supply 3 of the second of the two X-ray detector units provides at least one second supply voltage, adjusted to the at least one operating voltage of the at least one analysis unit 1 of the second X-ray detector unit.

A computing unit 45 is provided for controlling the medical imaging device 32 and/or for producing an X-ray image dataset based upon electrical signals processed by the detection unit 36, which signals are based on the incident X-ray radiation. In the case of a computed tomography device, the detection unit 36 usually acquires from a multiplicity of angular directions a (raw) X-ray image dataset of the object, which dataset is based on processed electrical pixel-measurement signals from the analysis unit 1. Then a mathematical method, for instance comprising filtered back-projection or an iterative reconstruction technique, can be used to reconstruct a final X-ray image dataset based upon the (raw) X-ray image dataset.

In addition, an input facility 47 and an output facility 49 are connected to the computing unit 45. The input facility 47 and the output facility 49 can allow, for example, interaction by a user, for instance manual configuration of an X-ray detector unit, confirmation or initiation of a method step.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector unit comprising:
   at least one analysis unit to process electrical signals delivered from a converter unit, the converter unit being coupled to the at least one analysis unit, and the at least one analysis unit being operatable by an operating voltage;
   an adjustable voltage supply to provide an adjustable supply voltage, the adjustable voltage supply being coupled to the at least one analysis unit;
   an identification unit to provide identification information about the at least one analysis unit in a readable manner, the identification unit being assigned to the at least one analysis unit; and
   a communication unit to:
      read the identification information provided from the identification unit, and adjust the adjustable voltage supply to equate the provided adjustable supply voltage to the operating voltage of the at least one analysis unit, the adjustable voltage supply being adjusted based on the identification information, and the communication unit being coupled to the adjustable voltage supply.

2. The X-ray detector unit of claim 1, wherein the adjustable voltage supply is configured to provide the adjustable supply voltage at between 1V and 7V.

3. The X-ray detector unit of claim 2, wherein
the communication unit includes a memory unit storing a look-up table; and
the communication unit is configured to derive an adjustment parameter for adjusting the adjustable voltage supply based on the identification information and a query to the look-up table.

4. The X-ray detector unit of claim 2, wherein the communication unit is configured to activate the at least one analysis unit once the adjustable supply voltage provided by the adjustable voltage supply is adjusted to the operating voltage of the at least one analysis unit.

5. The X-ray detector unit of claim 2, wherein the adjustable voltage supply is configured to provide a second voltage for operating the communication unit, the second voltage differing from the operating voltage of the at least one analysis unit.

6. The X-ray detector unit of claim 2, wherein the at least one analysis unit includes a plurality of analysis units operatable by the operating voltage, the adjustable voltage supply being configured to provide the operating voltage for the plurality of analysis units.

7. The X-ray detector unit of claim 1, wherein
the communication unit includes a memory unit storing a look-up table; and
the communication unit is configured to derive an adjustment parameter for adjusting the adjustable voltage supply based on the identification information and a query to the look-up table.

8. The X-ray detector unit of claim 1, wherein the communication unit is configured to activate the at least one analysis unit once the adjustable supply voltage provided by the adjustable voltage supply is adjusted to the operating voltage of the at least one analysis unit.

9. The X-ray detector unit of claim 1, wherein the adjustable voltage supply is configured to provide a second voltage for operating the communication unit, the second voltage differing from the operating voltage of the at least one analysis unit.

10. The X-ray detector unit of claim 1, wherein the at least one analysis unit includes a plurality of analysis units operatable by the operating voltage, the adjustable voltage supply being configured to provide the operating voltage for the plurality of analysis units.

11. An X-ray detector, comprising:
at least two X-ray detector units, each of the at least two X-ray detector units including an X-ray detector unit of claim 1, wherein
the adjustable voltage supply of a first X-ray detector unit among the at least two X-ray detector units is configured to provide a first supply voltage, the first supply voltage being adjusted to the operating voltage of the at least one analysis unit of the first X-ray detector unit, and
the adjustable voltage supply of a second X-ray detector unit among the at least two X-ray detector units is configured to provide a second supply voltage, the second supply voltage being adjusted to the operating voltage of the at least one analysis unit of the second X-ray detector unit.

12. A medical imaging device, comprising:
at least one X-ray detector unit, each of the at least one X-ray detector unit including an X-ray detector unit of claim 1; and
an X-ray source opposite the at least one X-ray detector unit, the X-ray source being configured to emit X-ray radiation onto the at least one X-ray detector unit.

13. The medical imaging device of claim 12, wherein the medical imaging device comprises a computed tomography device.

14. A medical imaging device, comprising:
an X-ray detector of claim 11; and
an X-ray source opposite the X-ray detector, the X-ray source being configured to emit X-ray radiation onto the X-ray detector.

15. The medical imaging device of claim 14, wherein the medical imaging device comprises a computed tomography device.

16. A method for operating an X-ray detector unit according to claim 1, the method comprising:
providing the identification information about the at least one analysis unit via the identification unit assigned to the at least one analysis unit;
reading the identification information from the identification unit via the communication unit;
automatically adjusting, via the communication unit, the provided adjustable supply voltage of the adjustable voltage supply to equate the provided adjustable supply voltage to the operating voltage of the at least one analysis unit, wherein the automatically adjusting adjusts the provided adjustable supply voltage based on the identification information; and
operating the at least one analysis unit using the adjustable supply voltage provided by the adjustable voltage supply.

17. The method of claim 16, wherein
the communication unit is configured to activate the at least one analysis unit; and
the at least one analysis unit is activatable by the communication unit only once the provided adjustable supply voltage is adjusted to the operating voltage of the at least one analysis unit.

* * * * *